(12) United States Patent
Shokoohi et al.

(10) Patent No.: US 6,331,190 B1
(45) Date of Patent: *Dec. 18, 2001

(54) ENDOLUMINAL VASCULAR PROSTHESIS

(75) Inventors: Mehrdad M. Shokoohi, Rancho Palos Verdes; Michael R. Henson; Gerard von Hoffmann, both of Trabuco Canyon, all of CA (US)

(73) Assignee: Endologix, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,411

(22) Filed: Jan. 14, 2000

Related U.S. Application Data

(63) Continuation of application No. 09/034,689, filed on Mar. 4, 1998, now Pat. No. 6,077,296.

(51) Int. Cl.[7] .................................................. A61F 2/00
(52) U.S. Cl. ........................................ 623/1.22; 623/1.16
(58) Field of Search ................................ 623/1.15, 1.16, 623/1.22

(56) References Cited

U.S. PATENT DOCUMENTS

| | | |
|---|---|---|
| 2,127,903 | 8/1938 | Bowen . |
| 2,845,959 | 8/1958 | Sidebotham . |
| 2,990,605 | 7/1961 | Demsyk . |
| 3,029,819 | 4/1962 | Starks . |
| 3,096,560 | 7/1963 | Liebig . |
| 3,805,301 | 4/1974 | Liebig . |
| 4,497,074 | 2/1985 | Rey et al. . |
| 4,501,263 | 2/1985 | Harbuck . |
| 4,503,568 | 3/1985 | Madras . |
| 4,592,754 | 6/1986 | Gupte et al. . |
| 4,617,932 | 10/1986 | Kornberg . |
| 4,816,028 | 3/1989 | Kapadia et al. . |
| 4,840,940 | 6/1989 | Sottiurai . |
| 4,856,516 | 8/1989 | Hillstead . |
| 4,878,906 | 11/1989 | Lindemann et al. . |
| 4,907,336 | 3/1990 | Gianturco . |
| 4,922,905 | 5/1990 | Strecker . |
| 4,994,071 | 2/1991 | MacGregor . |
| 5,019,909 | 5/1991 | Pinchuk . |
| 5,064,435 | 11/1991 | Porter . |
| 5,078,726 | 1/1992 | Kreamer . |
| 5,104,399 | 4/1992 | Lazarus . |
| 5,108,424 | 4/1992 | Hoffman, Jr. et al. . |
| 5,133,732 | 7/1992 | Wiktor . |
| 5,135,536 | 8/1992 | Hillstead . |
| 5,156,619 | 10/1992 | Ehrenfeld . |
| 5,178,634 | 1/1993 | Martinez . |
| 5,197,976 | 3/1993 | Herweck et al. . |
| 5,256,141 | 10/1993 | Gencheff et al. . |
| 5,275,622 | 1/1994 | Lazarus et al. . |
| 5,282,824 | 2/1994 | Gianturco . |
| 5,282,860 | 2/1994 | Matsuno et al. . |
| 5,304,200 | 4/1994 | Spaulding . |
| 5,314,444 | 5/1994 | Gianturco . |
| 5,314,472 | 5/1994 | Fontaine . |
| 5,316,023 | 5/1994 | Palmaz et al. . |
| 5,330,500 | 7/1994 | Song . |

(List continued on next page.)

FOREIGN PATENT DOCUMENTS

| | | |
|---|---|---|
| 282 175 B1 | 2/1988 | (EP) . |
| 323 176 | 12/1988 | (EP) . |
| 458 568 | 5/1991 | (EP) . |
| 0 177 330 B1 | 6/1991 | (EP) . |

(List continued on next page.)

Primary Examiner—Michael J. Milano
(74) Attorney, Agent, or Firm—Knobbe, Martens, Olson & Bear, LLP

(57) ABSTRACT

Disclosed is a tubular endoluminal vascular prosthesis, useful in treating, for example, an abdominal aortic aneurysm. The prosthesis comprises a self expandable wire support structure surrounded by a flexible tubular membrane. A delivery catheter and methods are also disclosed.

46 Claims, 12 Drawing Sheets

U.S. PATENT DOCUMENTS

| | | |
|---|---|---|
| 5,342,387 | 8/1994 | Summers . |
| 5,360,443 | 11/1994 | Barone et al. . |
| 5,366,504 | 11/1994 | Andersen et al. . |
| 5,370,683 | 12/1994 | Fontaine . |
| 5,387,235 | 2/1995 | Chuter . |
| 5,397,355 | 3/1995 | Marin et al. . |
| 5,405,377 | 4/1995 | Cragg . |
| 5,423,886 | 6/1995 | Arru et al. . |
| 5,425,765 | 6/1995 | Tiefenbrun et al. . |
| 5,443,498 | 8/1995 | Fontaine . |
| 5,443,500 | 8/1995 | Sigwart . |
| 5,456,713 | 10/1995 | Chuter . |
| 5,489,295 | 2/1996 | Piplani et al. . |
| 5,496,365 | 3/1996 | Sgro . |
| 5,507,767 | 4/1996 | Maeda et al. . |
| 5,507,771 | 4/1996 | Gianturco . |
| 5,522,880 | 6/1996 | Barone et al. . |
| 5,522,881 | 6/1996 | Lentz . |
| 5,522,883 | 6/1996 | Slater et al. . |
| 5,545,211 | 8/1996 | An et al. . |
| 5,554,181 | 9/1996 | Das . |
| 5,562,726 | 10/1996 | Chuter . |
| 5,562,728 | 10/1996 | Lazarus et al. . |
| 5,575,818 | 11/1996 | Pinchuk . |
| 5,578,072 | 11/1996 | Barone et al. . |
| 5,591,197 | 1/1997 | Orth et al. . |
| 5,593,417 | 1/1997 | Rhodes . |
| 5,609,625 | 3/1997 | Piplani et al. . |
| 5,609,627 | 3/1997 | Giocoechea et al. . |
| 5,628,783 | 5/1997 | Quiachon et al. . |
| 5,628,788 | 5/1997 | Pinchuk . |
| 5,632,772 | 5/1997 | Alcime et al. . |
| 5,641,373 | 6/1997 | Shannon et al. . |
| 5,643,339 | 7/1997 | Kavteladze et al. . |
| 5,647,857 | 7/1997 | Anderson et al. . |
| 5,653,727 | 8/1997 | Wiktor . |
| 5,653,743 | 8/1997 | Martin . |
| 5,653,746 | 8/1997 | Schmitt . |
| 5,653,747 | 8/1997 | Dereume . |
| 5,662,700 | 9/1997 | Lazarus . |
| 5,662,702 | 9/1997 | Keranen . |
| 5,665,115 | 9/1997 | Cragg . |
| 5,665,117 | 9/1997 | Keranen . |
| 5,674,241 | 10/1997 | Bley et al. . |
| 5,674,276 | 10/1997 | Andersen et al. . |
| 5,676,696 | 10/1997 | Marcade . |
| 5,676,697 | 10/1997 | McDonald . |
| 5,679,400 | 10/1997 | Tuch . |
| 5,681,346 | 10/1997 | Orth et al. . |
| 5,683,448 | 11/1997 | Cragg . |
| 5,683,449 | 11/1997 | Marcade . |
| 5,683,450 | 11/1997 | Goicoechea et al. . |
| 5,683,451 | 11/1997 | Lenker et al. . |
| 5,683,452 | 11/1997 | Barone et al. . |
| 5,683,453 | 11/1997 | Palmaz . |
| 5,690,644 | 11/1997 | Yurek et al. . |
| 5,693,066 | 12/1997 | Rupp et al. . |
| 5,693,084 | 12/1997 | Chuter . |
| 5,693,086 | 12/1997 | Goichoechea et al. . |
| 5,693,087 | 12/1997 | Parodi . |
| 5,693,088 | 12/1997 | Lazarus . |
| 5,695,516 | 12/1997 | Fischell et al. . |
| 5,695,517 | 12/1997 | Marin et al. . |
| 5,697,948 | 12/1997 | Marin et al. . |
| 5,716,365 | 2/1998 | Goicoechea et al. . |
| 5,716,393 | 2/1998 | Lindenberg . |
| 5,718,724 | 2/1998 | Goicoechea et al. . |
| 5,720,776 | 2/1998 | Chuter et al. . |
| 5,723,004 | 3/1998 | Dereume et al. . |
| 5,733,325 | 3/1998 | Robinson et al. . |
| 5,746,766 | 5/1998 | Edoga . |
| 5,746,776 | 5/1998 | Edoga . |
| 5,749,880 | 5/1998 | Banas et al. . |
| 5,755,770 | 5/1998 | Ravenscroft . |
| 5,755,771 | 5/1998 | Penn et al. . |
| 5,769,885 | 6/1998 | Quiachon et al. . |
| 5,769,887 | 6/1998 | Brown et al. . |
| 5,782,909 | 7/1998 | Quiachon et al. . |
| 5,810,836 | 9/1998 | Hussein et al. . |
| 5,824,037 | 10/1998 | Fogarty et al. . |
| 5,824,053 | 10/1998 | Khosravi et al. . |
| 5,843,160 | 12/1998 | Rhodes . |
| 5,843,164 | 12/1998 | Frantzen et al. . |
| 5,843,167 | 12/1998 | Dwyer et al. . |
| 5,851,228 | 12/1998 | Pinheiro . |
| 5,855,599 | 1/1999 | Wan . |
| 5,860,998 | 1/1999 | Robinson et al. . |
| 5,891,193 | 4/1999 | Robinson et al. . |
| 5,902,334 | 5/1999 | Dwyer et al. . |
| 5,928,279 | 7/1999 | Shannon et al. . |
| 5,935,161 | 8/1999 | Robinson et al. . |
| 5,938,696 | 8/1999 | Goicoechea et al. . |
| 5,957,973 | 9/1999 | Quiachon et al. . |
| 5,961,546 | 10/1999 | Robinson et al. . |
| 6,004,347 | 12/1999 | McNamara et al. . |
| 6,027,779 | 2/2000 | Campbell et al. . |
| 6,027,811 | 2/2000 | Campbell et al. . |
| 6,030,415 | 2/2000 | Chuter . |
| 6,039,749 | 3/2000 | Marin et al. . |
| 6,039,755 | 3/2000 | Edwin et al. . |
| 6,039,758 | 3/2000 | Quiachon et al. . |
| 6,051,020 | 4/2000 | Goicoechea et al. . |
| 6,070,589 | 6/2000 | Keith et al. . |
| 6,074,398 | 6/2000 | Leschinsky . |
| 6,077,296 | * 6/2000 | Shokoohi ........................ 623/1.15 |
| 6,077,297 | 6/2000 | Robinson et al. . |
| 6,117,167 | 9/2000 | Goicoechea et al. . |
| 6,123,722 | 9/2000 | Fogarty et al. . |
| 6,123,723 | 9/2000 | Konya et al. . |
| 6,126,685 | 10/2000 | Lenker et al. . |
| 6,129,756 | 10/2000 | Kugler et al. . |
| 6,168,610 | 1/2001 | Marin et al. . |
| 6,187,036 | * 2/2001 | Shaolian ........................ 623/1.15 |
| 6,192,944 | 2/2001 | Greenhalgh . |

FOREIGN PATENT DOCUMENTS

| | | |
|---|---|---|
| 0 596 145 A1 | 5/1994 | (EP) . |
| 0 621 015 A1 | 10/1994 | (EP) . |
| 689 806 | 5/1995 | (EP) . |
| 0 659 389 A1 | 6/1995 | (EP) . |
| 712 614 | 11/1995 | (EP) . |
| 732 088 | 3/1996 | (EP) . |
| 732 089 | 3/1996 | (EP) . |
| 974 314 | 3/1996 | (EP) . |
| 0 740 928 A2 | 11/1996 | (EP) . |
| 0 747 020 A2 | 12/1996 | (EP) . |
| 0 775 470 A1 | 5/1997 | (EP) . |
| 880 948 | 5/1998 | (EP) . |
| WO 93/13825 | 7/1993 | (WO) . |
| WO 94/24961 | 11/1994 | (WO) . |
| WO 96/41589 | 12/1996 | (WO) . |
| WO 97/10777 | 3/1997 | (WO) . |
| WO 97/14375 | 4/1997 | (WO) . |
| WO 97/19652 | 6/1997 | (WO) . |
| WO 98/02100 | 1/1998 | (WO) . |
| WO 97/10757 | 3/1999 | (WO) . |
| WO 99/44536 | 9/1999 | (WO) . |
| WO 99/47077 | 9/1999 | (WO) . |
| WO 99/58094 | 11/1999 | (WO) . |

* cited by examiner

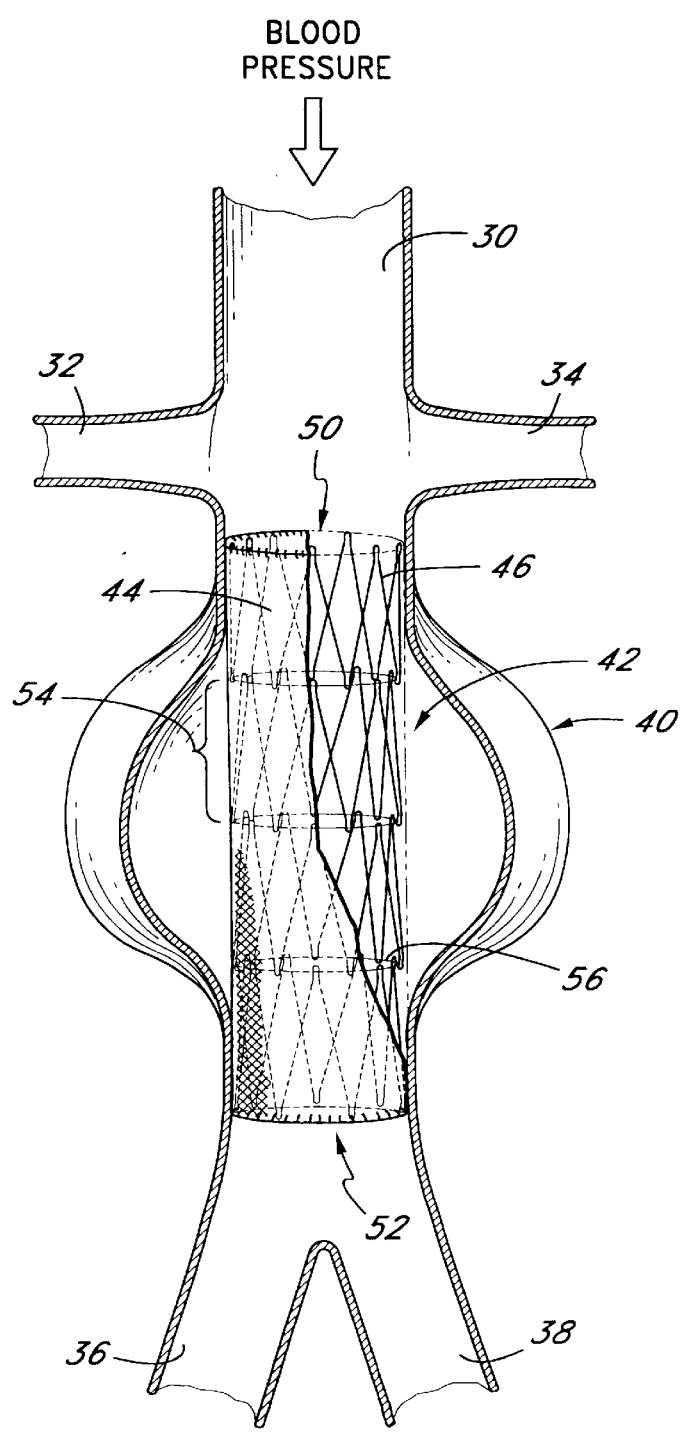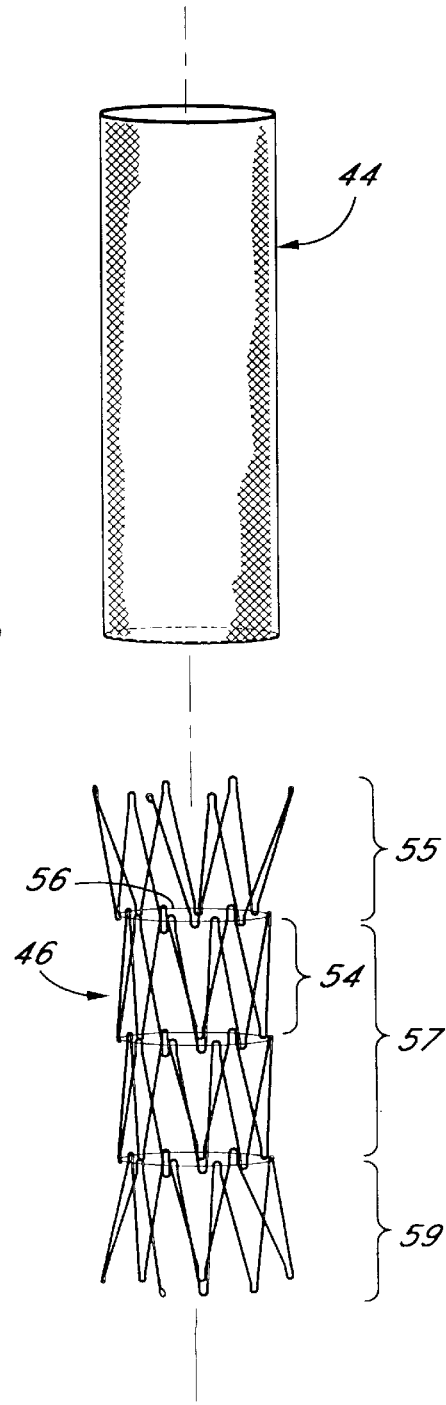

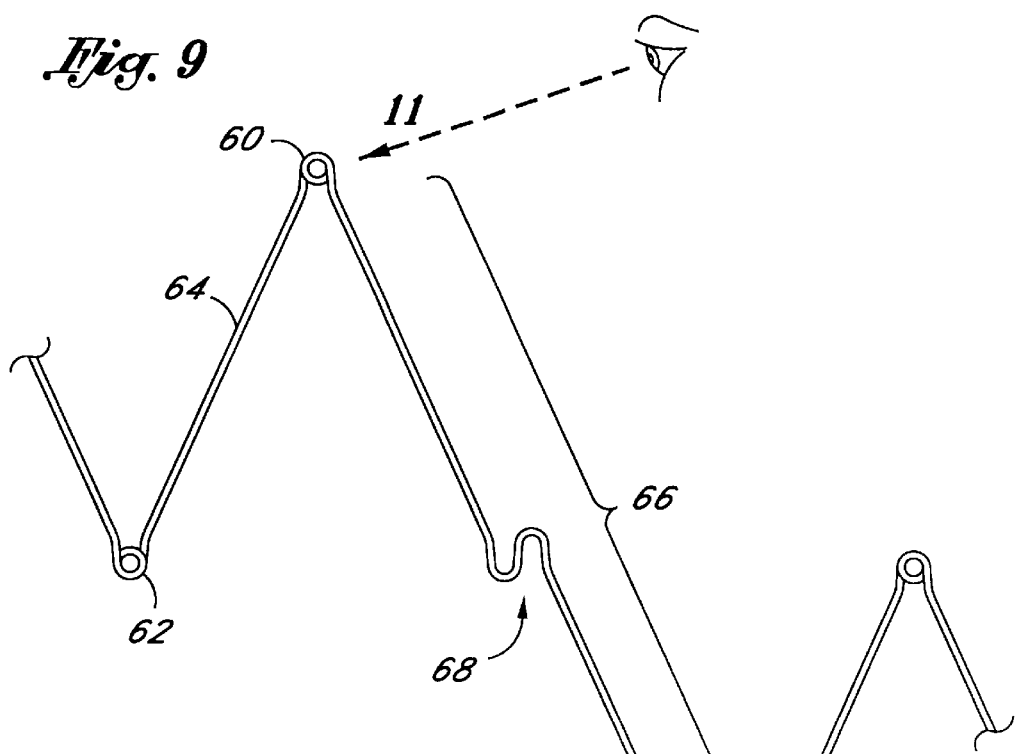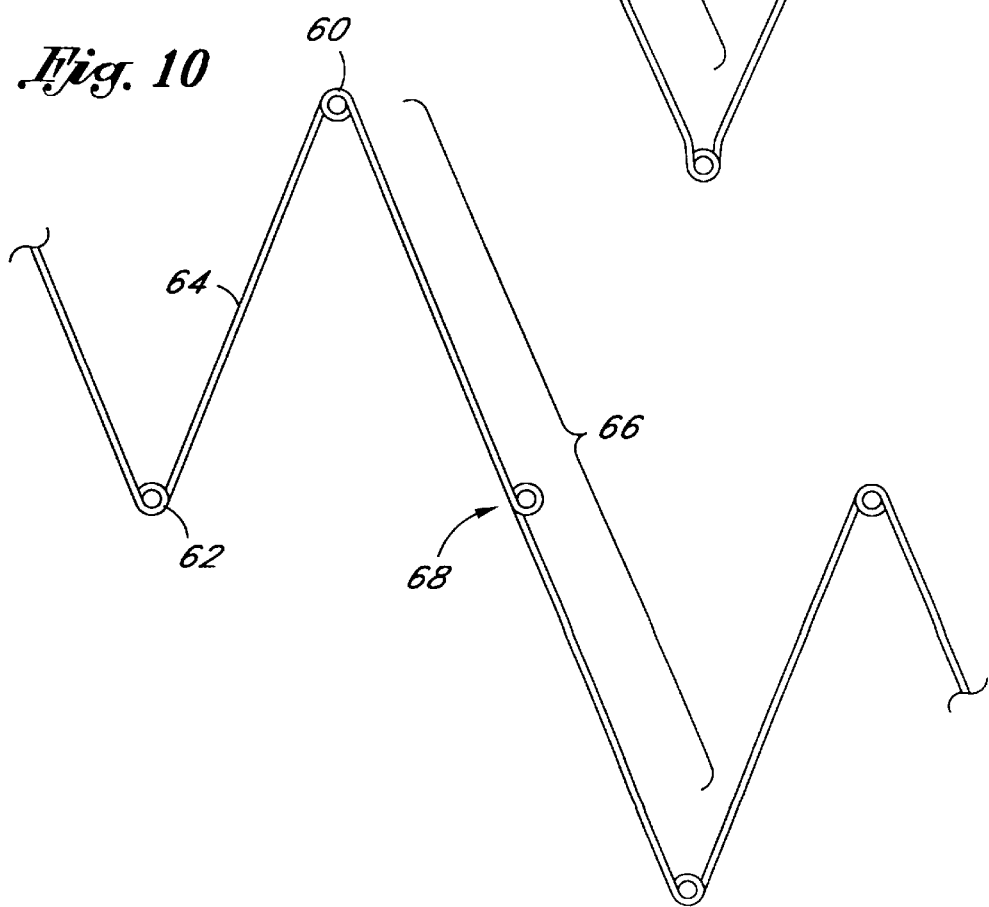

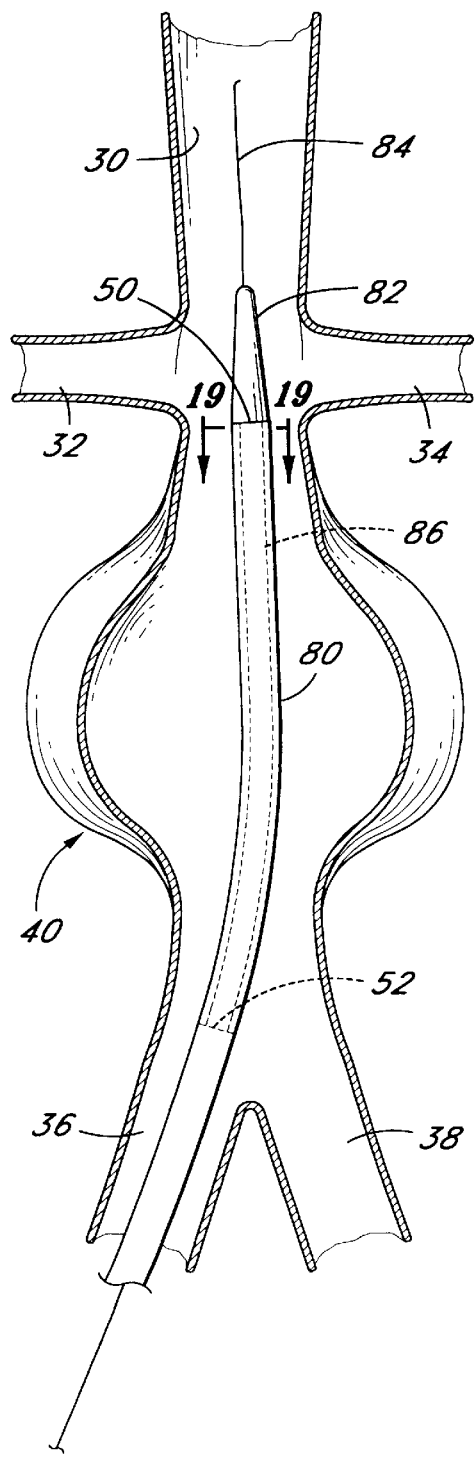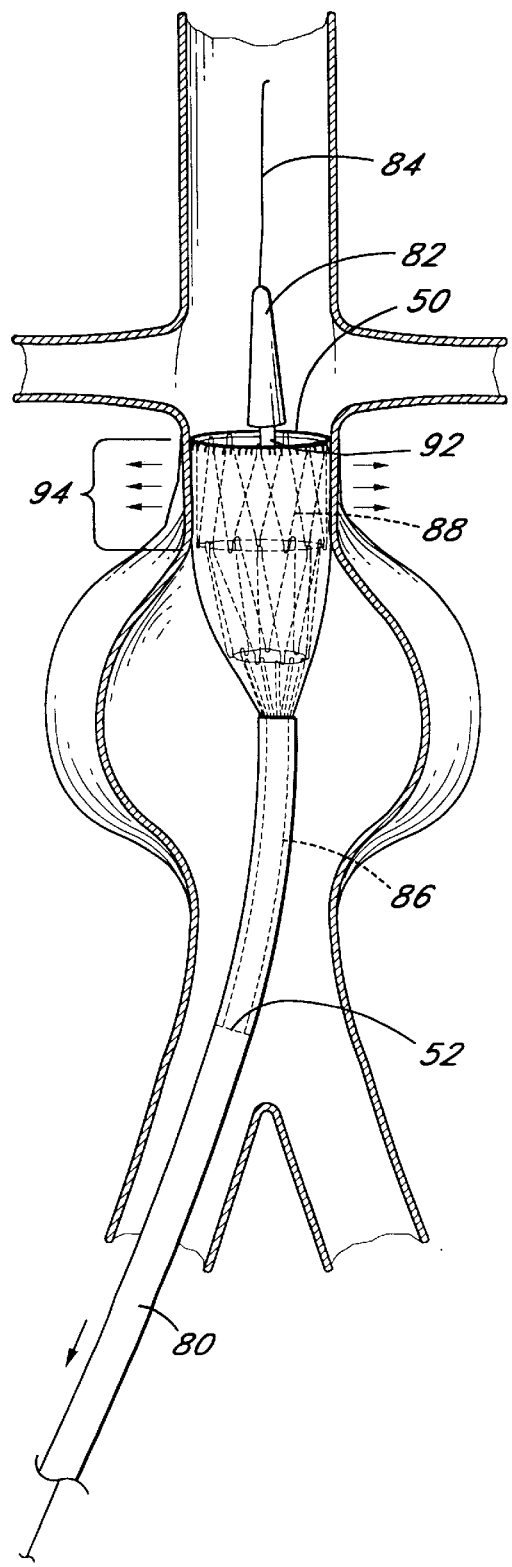
Fig. 17
Fig. 18

ENDOLUMINAL VASCULAR PROSTHESIS

This application is a continuation of U. S. application Ser. No. 09/034,689 filed on Mar. 4, 1998 now U. S. Pat. No. 6,077,296.

BACKGROUND OF THE INVENTION

The present invention relates to endoluminal vascular prostheses, and, in one application, to self-expanding endoluminal vascular prostheses for use in the treatment of abdominal aortic aneurysms.

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, P, DACRON®, TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. Since the graft must be secured, or sutured, to the remaining portion of the aorta, it is many times difficult to perform the suturing step because the thrombosis present on the remaining portion of the aorta, and that remaining portion of the aorta wall may many times be friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft in the endoluminal position (within the lumen of the artery). By this method, the graft is attached to the internal surface of an arterial wall by means of attachment devices (expandable stents), typically one above the aneurysm and a second stent below the aneurysm.

Stents permit fixation of a graft to the internal surface of an arterial wall without sewing or an open surgical procedure. Expansion of radially expandable stents is conventionally accomplished by dilating a balloon at the distal end of a balloon catheter. In U.S. Pat. No. 4,776,337, for example, Palmaz describes a balloon-expandable stent for endovascular treatments. Also known are self-expanding stents, such as described in U.S. Pat. No. 4,655,771 to Wallsten.

Notwithstanding the foregoing, there remains a need for a transluminally implantable endovascular prosthesis, such as for spanning an abdominal aortic aneurysm. Preferably, the tubular prosthesis can be self expanded at the site to treat the abdominal aortic aneurysm.

SUMMARY OF THE INVENTION

There is provided in accordance with one aspect of the present invention an endoluminal prosthesis. The endoluminal prosthesis comprises a tubular wire support having a proximal end, a distal end and central lumen extending therethrough. The wire support comprises at least a first and a second axially adjacent tubular segments, joined by a connector extending therebetween. The first and second segments and the connector are formed from a single length of wire.

In one embodiment, the wire in each segment comprises a series of proximal bends, a series of distal bends, and a series of wall (strut) segments connecting the proximal bends and distal bends to form a tubular segment wall. Preferably, at least one proximal bend on a first segment is connected to at least one corresponding distal bend on a second segment. The connection may be provided by a metal link, a suture, or other connection means known in the art.

Preferably, the endoluminal prosthesis further comprises a polymeric layer such as a tubular PTFE sleeve, on the support.

In accordance with another aspect of the present invention, there is provided a method of making an endoluminal prosthesis. The method comprises the steps of providing a length of wire, and forming the wire into two or more zig zag sections, each zig zag section connected by a link. The formed wire is thereafter rolled about an axis to produce a series of tubular elements positioned along the axis such that each tubular element is connected to the adjacent tubular element by a link. Preferably, the method further comprises the step of positioning a tubular polymeric sleeve concentrically on at least a portion of the endoluminal prosthesis.

In accordance with another aspect of the present invention, there is provided a multizone endoluminal prosthesis. The multizone prosthesis comprises a tubular wire support having a proximal end, a distal end and a central lumen extending therethrough. The wire support comprises at least a first and a second axially adjacent tubular segments, joined by a connector extending therebetween. The first tubular segment has a different radial strength than the second tubular segment. In one embodiment, the prosthesis further comprises a third tubular segment. At least one of the tubular segments has a different radial strength than the other two tubular segments. In another embodiment, a proximal end of the prosthesis is self expandable to a greater diameter than a central region of the prosthesis.

In accordance with another aspect of the present invention, there is provided an endoluminal prosthesis. The prosthesis comprises an elongate flexible wire, formed into a plurality of axially adjacent tubular segments spaced along an axis. Each tubular segment comprises a zig zag section of wire, having a plurality of proximal bends and distal bends, with the wire continuing between each adjacent tubular segment creating an integral structural support system throughout the longitudinal length of the device. The prosthesis is radially collapsible into a first, reduced cross sectional configuration for implantation into a body lumen, and self expandable to a second, enlarged cross sectional configuration at a treatment site in a body lumen.

Preferably, the prosthesis further comprises an outer tubular sleeve surrounding at least a portion of the prosthesis. One or more lateral perfusion ports may be provided through the tubular sleeve.

In one embodiment, the prosthesis has an expansion ratio of at least about 1:5, and, preferably at least about 1:6. The prosthesis in another embodiment has an expanded diameter of at least about 20 mm in an unconstrained expansion, and the prosthesis is implantable using a catheter no greater than about 16 French. Preferably, the prosthesis has an expanded diameter of at least about 25 mm, and is implantable on a delivery device having a diameter of no more than about 16 French.

In accordance with a further aspect of the present invention, there is provided a method of implanting an endoluminal vascular prosthesis. The method comprises the steps of providing a self expandable endoluminal vascular prosthesis, having a proximal end, a distal end, and a central lumen extending therethrough. The prosthesis is expandable from a first, reduced diameter to a second, enlarged diameter. The prosthesis is mounted on a catheter, such that when the prosthesis is in the reduced diameter configuration on the catheter, the catheter diameter through the prosthesis is no more than about 16 French. The catheter is thereafter introduced into the body lumen and positioned such that the prosthesis is at a treatment site in the body lumen. The prosthesis is released at the treatment site, such that it expands from the first diameter to the second diameter, wherein the second diameter is at least about 20 mm.

Further features and advantages of the present invention will become apparent to those of ordinary skill in the art in view of the disclosure herein, when considered together with the attached drawings and claims.

BRIEF DESCRIPTION OF THE DRAWINGS

FIG. 1 is a schematic representation of an endoluminal vascular prosthesis in accordance with the present invention, positioned within a symmetric abdominal aortic aneurysm.

FIG. 2 is an exploded view of an endoluminal vascular prosthesis in accordance with the present invention, showing a self expandable wire support structure separated from an outer tubular sleeve.

FIG. 9 is a fragmentary view of an alternate wire layout in accordance with a further aspect of the present invention.

FIG. 10 is a fragmentary view of an alternate wire layout in accordance with a further aspect of the present invention.

FIG. 17 is a schematic illustration of a delivery catheter in accordance with the present invention, positioned within an abdominal aortic aneurysm.

FIG. 18 is an illustration as in FIG. 17, with the endoluminal prosthesis partially deployed from the delivery catheter.

DETAILED DESCRIPTION OF THE PREFERRED EMBODIMENT

Figure 3:
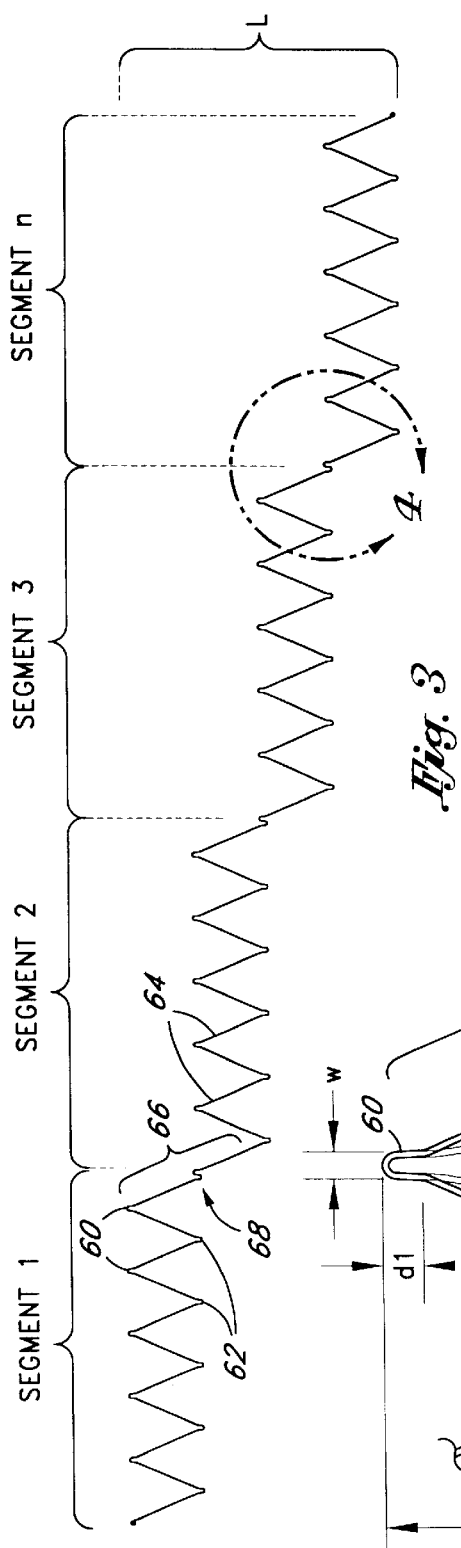
FIG. 3 is a plan view of a formed wire useful for rolling about an axis into a multi-segment support structure in accordance with the present invention.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification. A generally symmetrical aneurysm 40 is illustrated in the infrarenal portion of the diseased aorta. An expanded endoluminal vascular prosthesis 42, in accordance with the present invention, is illustrated spanning the aneurysm 40. Although features of the endoluminal vascular prosthesis of the present invention can be modified for use in a bifurcation aneurysm, such as the common iliac bifurcation, the endoluminal prosthesis of the present invention will be described herein primarily in terms of its application in the straight segment of the abdominal aorta, or Thoracic or iliac arteries.

The endoluminal vascular prosthesis 42 includes a polymeric sleeve 44 and a tubular wire support 46, which are illustrated in situ in FIG. 1. The sleeve 44 and wire support 46 are more readily visualized in the exploded view shown in FIG. 2. The endoluminal prosthesis 42 illustrated and described herein depicts an embodiment in which the polymeric sleeve 44 is situated concentrically outside of the tubular wire support 46. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 44 is inside or outside the wire support 46, the sleeve may be attached to the wire support by any of a variety of means, including laser bonding, adhesives, clips, sutures, dipping or spraying or others, depending upon the composition of the sleeve 44 and overall graft design.

The polymeric sleeve 44 may be formed from any of a variety of synthetic polymeric materials, or combinations thereof, including PTFE, PE, PET, Urethane, Dacron, nylon, polyester or woven textiles. Preferably, the sleeve material exhibits relatively low inherent elasticity, or low elasticity out to the intended enlarged diameter of the wire cage 46. The sleeve material preferably has a thin profile, such as no larger than about 0.002 inches to about 0.005 inches.

In a preferred embodiment of the invention, the material of sleeve 44 is sufficiently porous to permit ingrowth of endothelial cells, thereby providing more secure anchorage of the prosthesis and potentially reducing flow resistance, sheer forces, and leakage of blood around the prosthesis. Porosity in polymeric sleeve materials may be estimated by measuring water permeability as a function of hydrostatic pressure, which will preferably range from about 3 to 6 psi.

The porosity characteristics of the polymeric sleeve 44 may be either homogeneous throughout the axial length of the prosthesis 42, or may vary according to the axial position along the prosthesis 42. For example, referring to FIGS. 1 and 2, different physical properties will be called upon at different axial positions along the prosthesis 42 in use. At least a proximal portion 55 and a distal portion 59 of the prosthesis 42 will seat against the native vessel wall, proximally and distally of the aneurysm. In these proximal and distal portions, the prosthesis preferably encourages endothelial growth, or, at least, permits endothelial growth to infiltrate portions of the prosthesis in order to enhance anchoring and minimize leakage. A central portion 57 of the prosthesis spans the aneurysm, and anchoring is less of an issue. Instead, minimizing blood flow through the prosthesis wall becomes a primary objective. Thus, in a central zone 57 of the prosthesis 42, the polymeric sleeve 44 may either be nonporous, or provided with pores of no greater than about 60% to 80%.

A multi-zoned prosthesis 42 may also be provided in accordance with the present invention by positioning a tubular sleeve 44 on a central portion 57 of the prosthesis, such that it spans the aneurysm to be treated, but leaving a proximal attachment zone 55 and a distal attachment zone 59 of the prosthesis 42 having exposed wires from the wire support 46. In this embodiment, the exposed wires 46 are positioned in contact with the vessel wall both proximally and distally of the aneurysm, such that the wire, over time, becomes embedded in cell growth on the interior surface of the vessel wall.

In one embodiment of the prosthesis 42, the sleeve 44 and/or the wire support 46 is tapered, having a relatively larger expanded diameter at the proximal end 50 compared to the distal end 52. The tapered design may allow the prosthesis to conform better to the natural decreasing distal cross section of the vessel, to reduce the risk of graft migration and potentially create better flow dynamics.

Figure 5:
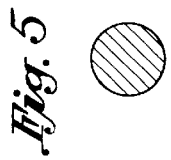
FIG. 5 is a cross sectional view taken along the lines 5—5 of FIG. 4.
Figure 6:
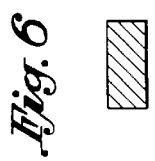
FIG. 6 is an alternate cross sectional view taken along the lines 5—5 of FIG. 4.

The tubular wire support 46 is preferably formed from a continuous single length of round (shown in FIG. 5) or flattened (shown in FIG. 6) wire. The wire support 46 is preferably formed in a plurality of discrete segments 54, connected together and oriented about a common axis. Each pair of adjacent segments 54 is connected by a connector 66 as will be discussed. The connectors 66 collectively produce a generally axially extending backbone which adds axial strength to the prosthesis 42. Adjacent segments can be connected both by the backbone, as well as by other structures, including circumferentially extending sutures 56 (illustrated in FIGS. 1 and 2), solder joints, wire loops and any of a variety of interlocking relationships. The suture can be made from any of a variety of biocompatible polymeric materials or alloys, such as nylon, polypropylene, or stainless steel. Other means of securing the segments 54 to one another are discussed below (see FIG. 8).

The segmented configuration of the tubular wire support 46 facilitates a great deal of flexibility. Each segment 54, though joined to adjacent segments, may be independently engineered to yield desired parameters. Each segment may range in axial length from about 0.3 to about 5 cm. Generally, the shorter their length the greater the radial strength. An endoluminal prosthesis may include from about 1 to about 50 segments, preferably from about 3 to about 10 segments. For example, while a short graft patch, in accordance with the invention, may comprise only 2 segments and span a total of 2 to 3 cm, a complete graft may comprise 4 or more segments and span the entire aortic aneurysm. In addition to the flexibility and other functional benefits available through employment of different length segments, further flexibility can be achieved through adjustments in the number, angle, or configuration of the wire bends associated with the tubular support. Potential bend configurations are discussed in greater detail below (see FIGS. 4–16).

A variety of additional advantages can be achieved through the multi-segment configuration of the present invention. For example, referring to FIG. 2, the wire cage 46 is dividable into a proximal zone 55, a central zone 57 and a distal zone 59. As has been discussed, the wire cage 46 can be configured to taper from a relatively larger diameter in the proximal zone 55 to a relatively smaller diameter in the distal zone 59. In addition, the wire cage 46 can have a transitional tapered and or stepped diameter within a given zone.

The cage 46 can also be provided with a proximal zone 55 and distal zone 59 that have a larger relative expanded diameter than the central zone 57, as illustrated in FIG. 2. This configuration may desirably resist migration of the prosthesis within the vessel. The proximal zone 55 and/or distal zone 59 can be left without an outer covering 44, with the outer sleeve 44 covering only the central zone 57. This permits the proximal and distal zones 55, 59 to be in direct contact with tissue proximally and distal to the lesion, which may facilitate endothelial cell growth.

In addition to having differing expanded diameters in different zones of the prosthesis 42, different zones can be provided with a different radial expansion force, such as ranging from about 0.2 lbs to about 0.8 lbs. In one embodiment, the proximal zone 55 is provided with a greater radial force than the central zone 57 and/or distal zone 59. The greater radial force can be provided in any of a variety of manners discussed elsewhere herein, such as through the use of an additional one or two or three or more proximal bends 60, distal bends 62 and wall sections 64 compared to a reference segment 54 in the central zone 57 or distal zone 59. Alternatively, additional spring force can be achieved in the proximal zone 55 through the use of the same number of proximal bends 60 as in the rest of the prosthesis, but with a heavier gauge wire. Radial force beyond the expanded diameter limit of the central zone 57 can be achieved by tightening the suture 56 as illustrated in FIG. 2 such that the central zone 57 is retained under compression even in the expanded configuration. By omitting a suture at the proximal end and/or distal end of the prosthesis, the proximal end and distal end will flair radially outwardly to a fully expanded configuration as illustrated in FIG. 2.

The wire may be made from any of a variety of different alloys, such as elgiloy, nitinol or MP35N, or other alloys which include nickel, titanium, tantalum, or stainless steel, high Co—Cr alloys or other temperature sensitive materials. For example, an alloy comprising Ni 15%, Co 40%, Cr 20%, Mo 7% and balance Fe may be used. The tensile strength of suitable wire is generally above about 300 K psi and often between about 300 and about 340 K psi for many embodiments. In one embodiment, a Chromium-Nickel-Molybdenum alloy such as that marketed under the name Conichrom (Fort Wayne Metals, Indiana) has a tensile strength ranging from 300 to 320 K psi, elongation of 3.5–4.0% and breaking load at approximately 80 lbs to 70 lbs. The wire may be treated with a plasma coating and be provided with/without coating such as: PTFE, Teflon, Perlyne and Drugs.

In addition to segment length and bend configuration, discussed above, another determinant of radial strength is wire gauge. The radial strength, measured at 50% of the collapsed profile, preferably ranges from about 0.2 lb to 0.8 lb, and generally from about 0.4 lb to about 0.5 lb. or more. Preferred wire diameters in accordance with the present invention, range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters (such as the number of struts, or proximal bends 60 and distal bends 62 per segment), as will be discussed. A wire diameter of approximately 0.018 inches may be useful in a graft having four segments each having 2.5 cm length per segment, each segment having six struts intended for use in the aorta, while a smaller diameter such as 0.006 inches might be useful for a 0.5 cm segment graft having 5 struts per segment intended for the iliac artery. The length of cage 42 could be as long as about 28 cm.

In one embodiment of the present invention, the wire diameter is tapered from the proximal to distal ends. Alternatively, the wire diameter may be tapered incrementally or stepped down, or stepped up, depending on the radial strength requirements of each particular clinical application. In one embodiment, intended for the abdominal aortic artery, the wire has a cross section of about 0.018 inches in the proximal zone 55 and the wire tapers down to a diameter of about 0.006 inches in the distal zone 59 of the graft 42. End point dimensions and rates of taper can be varied widely, within the spirit of the present invention, depending upon the desired clinical performance.

Referring to FIG. 3, there is illustrated a plan view of the single formed wire used for rolling about a longitudinal axis to produce a four segment tubular wire support. The formed wire exhibits distinct segments, each corresponding to an individual tubular segment 54 in the tubular support (see FIGS. 1 and 2).

Each segment has a repeating pattern of proximal bends 60 connected to corresponding distal bends 62 by wall sections 64 which extend in a generally zig zag configuration when the segment 54 is radially expanded. Each segment 54 is connected to the adjacent segment 54 through a connector 66, except at the terminal ends of the graft. The connector 66 in the illustrated embodiment comprises two wall sections 64 which connect a proximal bend 60 on a first segment 54 with a distal bend 62 on a second, adjacent segment 54. The connector 66 may additionally be provided with a connector bend 68, which may be used to impart increased radial strength to the graft and/or provide a tie site for a circumferentially extending suture.

Figure 4:
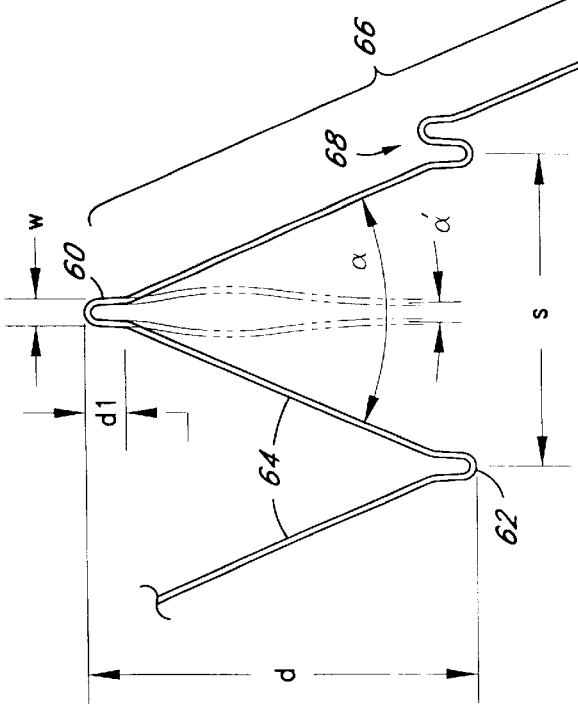
FIG. 4 is an enlarged detail view of a portion of the formed wire illustrated in FIG. 3.

Referring to FIG. 4, there is shown an enlarged view of the wire support illustrating a connector 66 portion between adjacent segments 54. In the embodiment shown in FIG. 4, a proximal bend 60 comprises about a 180 degree arc, having a radial diameter of (w) (Ranging from 0.070 to 0.009 inches), depending on wire diameter followed by a relatively short length of parallel wire spanning an axial distance of d1. The parallel wires thereafter diverge outwardly from one another and form the strut sections 64, or the proximal half of a connector 66. At the distal end of the strut sections 64, the wire forms a distal bend 62, preferably having identical characteristics as the proximal bend 60, except being concave in the opposite direction. The axial direction component of the distance between the apices of the corresponding proximal and distal bends 60, 62 is referred to as (d) and represents the axial length of that segment. The total expanded angle defined by the bend 60 and the divergent strut sections 64 is represented by $\alpha$. Upon compression to a collapsed state, such as when the graft is within the deployment catheter, the angle $\alpha$ is reduced to $\alpha'$. In the expanded configuration, $\alpha$ is generally within the range of from about 35° to about 45°. The expanded circumferential distance between any two adjacent distal bends 62 (or proximal bends 60) is defined as (s).

In general, the diameter W of each proximal bend 60 or distal bend 62 is within the range of from about 0.009 inches to about 0.070 inches depending upon the wire diameter. Diameter W is preferably as small as possible for a given wire diameter and wire characteristics. As will be appreciated by those of skill in the art, as the distance W is reduced to approach two times the cross section of the wire, the bend 60 or 62 will exceed the elastic limit of the wire, and radial strength of the finished segment will be lost. Determination of a minimum value for W, in the context of a particular wire diameter and wire material, can be readily determined through routine experimentation by those of skill in the art. Similarly, although at least some distance of d1 is desired, from the apex to the first bend in the wall section 64, the distance d1 is preferably minimized within the desired radial strength performance requirements. As d1 increases, it may disadvantageously increase the collapsed profile of the graft.

As will be appreciated from FIGS. 3 and 4, the sum of the distances (s) in a plane transverse to the longitudinal axis of the finished graft will correspond to the circumference of the finished graft in that plane. For a given circumference, the number of proximal bends 60 or distal bends 62 is directly related to the distance (s) in the corresponding plane. Preferably, the finished graft in any single transverse plane will have from about 3 to about 10 (s) dimensions, preferably from about 4 to about 8 (s) dimensions and, more preferably, about 5 or 6 (s) dimensions for an aortic application. Each (s) dimension corresponds to the distance between any two adjacent bends 60—60 or 62—62 as will be apparent from the discussion herein. Each segment 54 can thus be visualized as a series of triangles extending circumferentially around the axis of the graft, defined by a proximal bend 60 and two distal bends 62 or the reverse.

By modifying wire support parameters (such as d, d1, s, alpha and alpha'), the manufacturer enjoys tremendous design control with respect to the total axial length, axial and radial flexibility, radial force and expansion ratios, and consequently prosthesis performance. For example, an increase in the dimension (w) translates directly into an increased collapsed profile since the circumference of the collapsed profile can be no smaller than the sum of the distances (w) in a given transverse plane. Similarly, an increase in the number of proximal bends 60 in a given segment may increase radial strength, but will similarly increase the collapsed profile. Since the primary radial force comes from the proximal bends 60 and distal bends 62, the wall sections 64 act as a lever arm for translating that force into radial strength. As a consequence, decreasing the length of strut sections 64 for a given number of proximal bends 60 will increase the radial strength of the segment but call for additional segments to maintain overall graft length. Where a minimal entry profile is desired, radial strength is best accomplished by decreasing the length of wall sections 64 rather than increasing the number of proximal bends 60. On the other hand, increasing the number of (shorter) segments 54 in a given overall length graft will increase the degree of axial shortening upon radial expansion of the graft. Thus, in an embodiment where axial shortening is to be avoided, increased radial strength may be optimized through selection of wire material or wire gauge and other parameters, while minimizing the number of total segments in the graft. Other geometry consequences of the present invention will be apparent to those of skill in the art in view of the disclosure herein.

Figure 8:
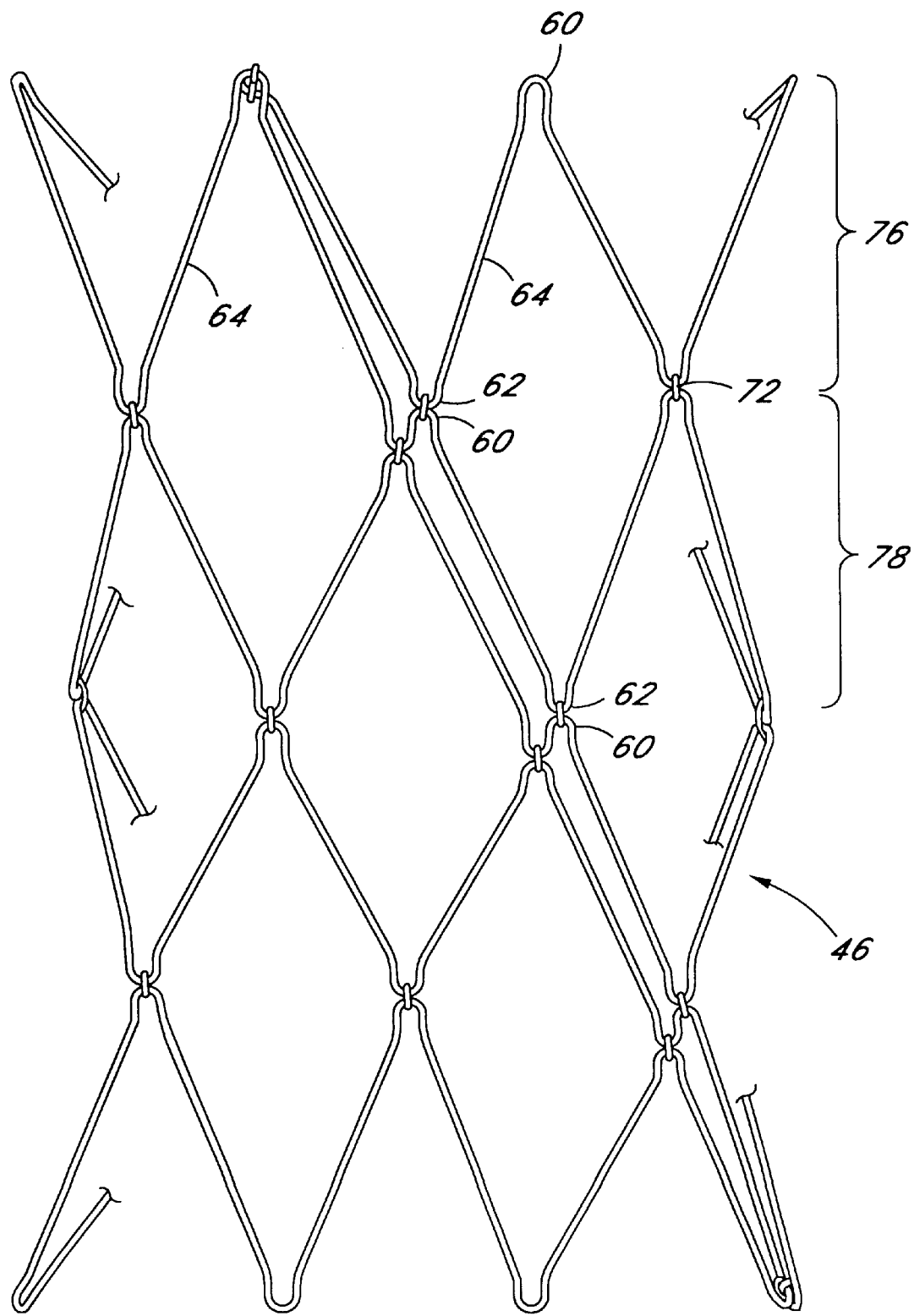
FIG. 8 is an elevational view of a crosslinked wire layout in accordance with the present invention.
Figure 8A:
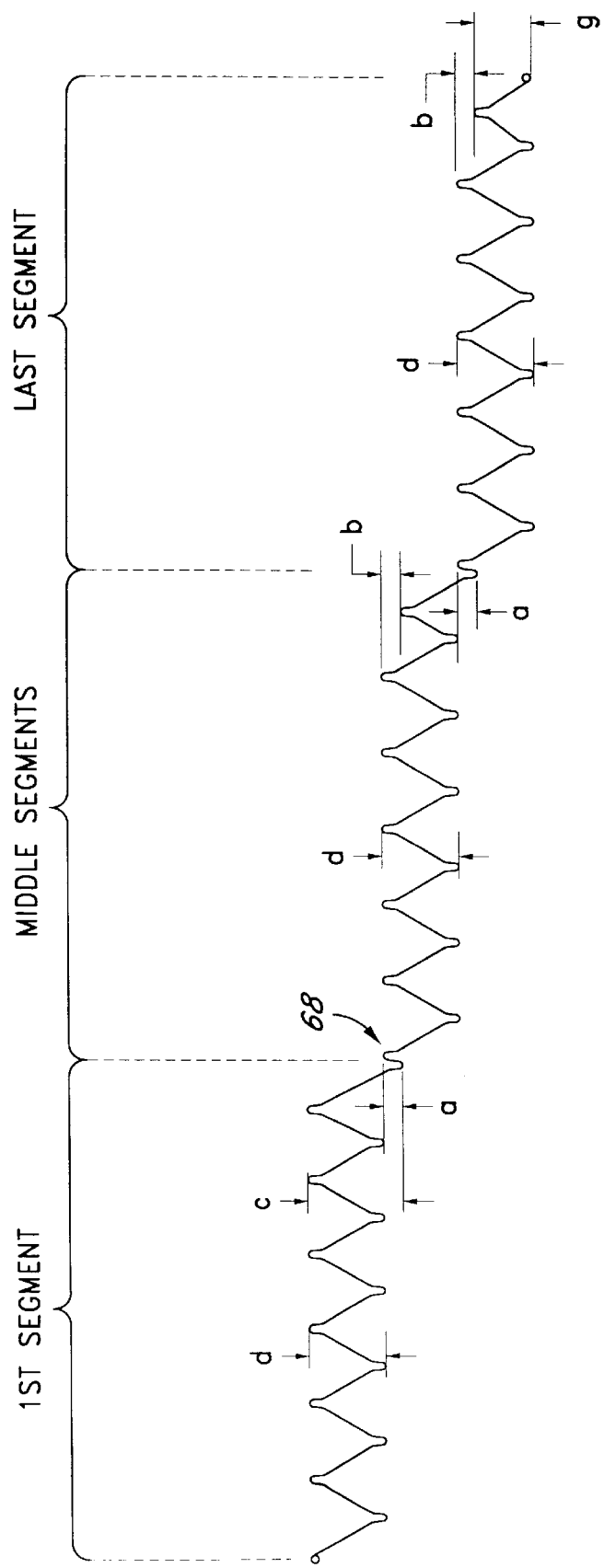
FIG. 8A is a plan view of a formed wire layout useful for forming the crosslinked embodiment of FIG. 8.
Figure 11:
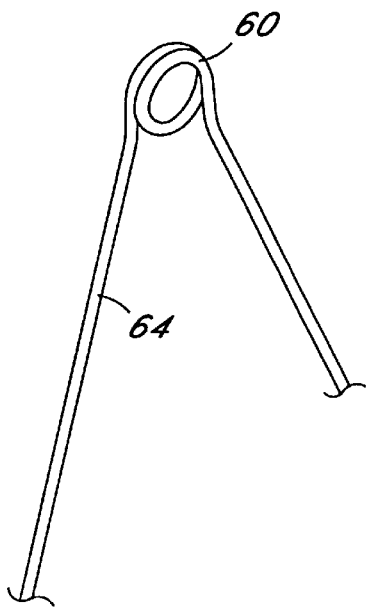
FIG. 11 is a fragmentary view of an apex in accordance with one aspect of the present invention.
Figure 12:
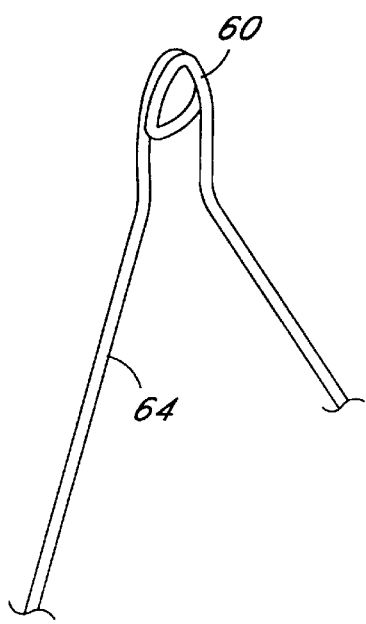
FIG. 12 is a fragmentary view of an alternate embodiment of an apex in accordance with the present invention.

In one embodiment of the type illustrated in FIG. 8A, w is about 2.0 mm±1 mm for a 0.018 inch wire diameter. D1 is about 3 mm±1 mm, d is about 20 mm±1 mm, c is about 23 mm±1 mm, g is about 17 mm,±1 mm, a is about 3 mm±1 mm and b is about 3 mm±1 mm. Specific dimensions for all of the foregoing variables can be varied considerably, depending upon the desired wire configuration, in view of the disclosure herein.

Figure 7:
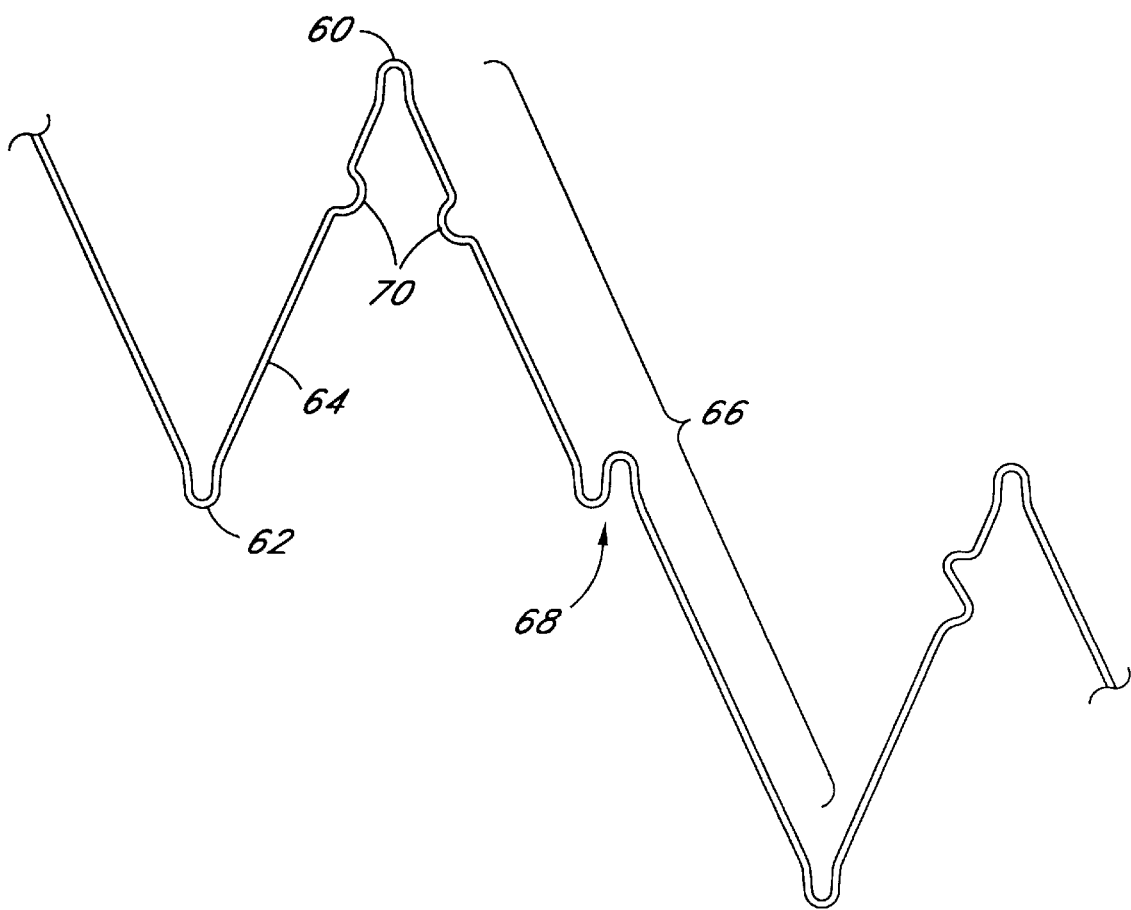
FIG. 7 is a fragmentary view of an alternate wire layout in accordance with a further aspect of the present invention.

Referring to FIG. 7, there is shown an alternative wire layout having a plurality of radiussed bends 70 in one or more sections of strut 64 which may be included to provide additional flex points to provide enhanced fluid dynamic characteristics and maintain the tubular shape.

In another embodiment of the wire support, illustrated in FIG. 8, each pair of adjacent proximal and distal segments, 76 and 78, may be joined by crosslinking of the corresponding proximal and distal bends. Thus, a proximal bend 60 from a distal segment 78 is connected to the corresponding distal bend 62 of a proximal segment 76, thereby coupling the proximal segment 76 and distal segment 78. The connection between corresponding proximal bends 60 and distal bends 62 can be accomplished in any of a variety of ways as will be apparent to those of skill in the art in view of the disclosure herein. In the illustrated embodiment, the connection is accomplished through the use of a link 72. Link 72 may be a loop of metal such as stainless steel, a suture, a welded joint or other type of connection. Preferably, link 72 comprises a metal loop or ring which permits pivotable movement of a proximal segment 76 with respect to a distal segment 78.

In one example of an endoluminal vascular prosthesis in accordance with the present invention, the proximal segment 76 is provided with six distal bends 62. The corresponding distal segment 78 is provided with six proximal bends 60 such that a one to one correspondence exists. A link 72 may be provided at each pair of corresponding bends 60, 62, such that six links 72 exist in a plane transverse to the longitudinal axis of the graft at the interface between the proximal segment 76 and the distal segment 78. Alternatively, links 72 can be provided at less than all of the corresponding bends, such as at every other bend, every third bend, or only on opposing sides of the graft. The distribution of the links 72 in any given embodiment can be selected to optimize the desired flexibility characteristics and other performance criteria in a given design.

The use of connectors such as cross link 72 enables improved tracking of the graft around curved sections of the vessel. In particular, the wire cage 46 as illustrated in FIG. 8 can be bent around a gentle curve, such that it will both retain the curved configuration and retain patency of the central lumen extending axially therethrough. The embodiment illustrated in FIG. 2 may be more difficult to track curved anatomy while maintaining full patency of the central lumen. The ability to maintain full patency while extending around a curve may be desirable in certain anatomies, such as where the aorta fails to follow the linear infrarenal path illustrated in FIG. 1.

Referring to FIG. 8a, there is illustrated a plan view of a formed wire useful for rolling about an axis to produce a multi-segmented support structure of the type illustrated in FIG. 8. In general, the formed wire of FIG. 8a is similar to that illustrated in FIG. 3. However, whereas any given pair of corresponding distal bends 62 and proximal bends 60 of the embodiment of FIG. 3 overlap in the axial direction to facilitate threading a circumferential suture therethrough, the corresponding distal bend 62 and proximal bend 60 of the embodiment illustrated in FIG. 8a may abut end to end against each other or near each other as illustrated in FIG. 8 to receive a connector 72 thereon.

The appropriate axial positioning of a distal bend 62 with respect to a corresponding proximal bend 60 can be accomplished in a variety of ways, most conveniently by appropriate formation of the connector bend 68 between adjacent segments of the wire cage.

Figure 13:
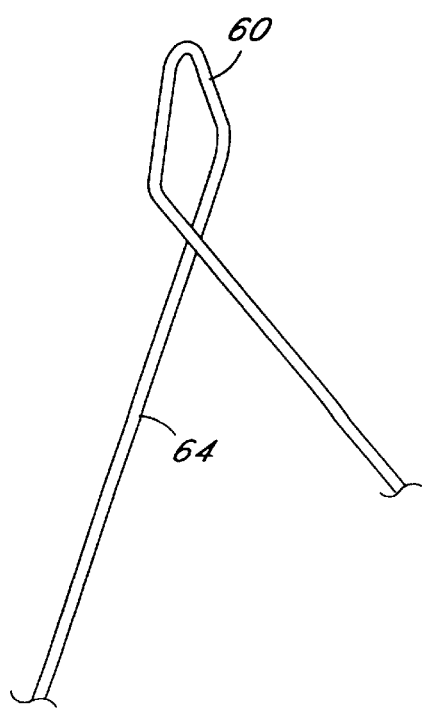
FIG. 13 is a further embodiment of an apex in accordance with the present invention.

FIGS. 9–16 illustrate alternative bend configurations in accordance with the present invention. FIG. 9 shows one embodiment having the proximal and distal bends as eyelets, but the connector bend 68, remaining in the usual configuration. The embodiment illustrated in FIG. 10 has the proximal and distal bends as well as the connector bend in the eyelet configuration. Various eyelet designs in accordance with the present invention are shown in greater detail in FIGS. 11–13, including a double-looped circular eyelet (FIG. 11), a double-looped triangular eyelet (FIG. 12), and a single-looped triangular eyelet (FIG. 13). The eyelets can be used to receive a circumferentially extending suture or wire as has been described.

Figure 14:
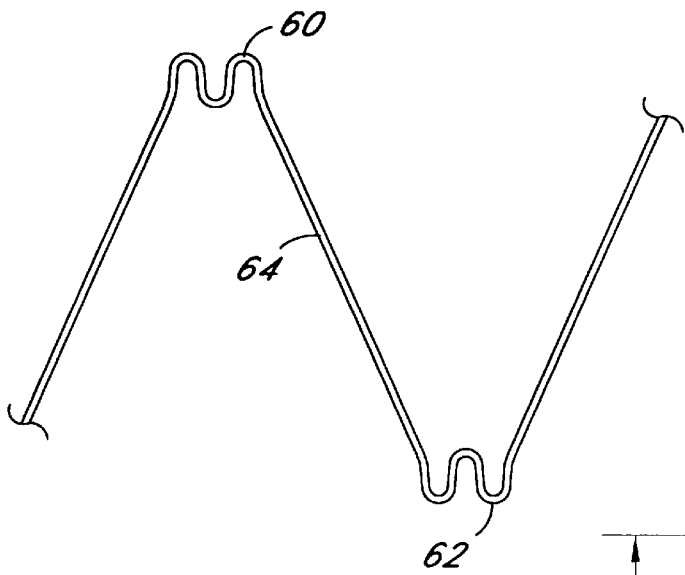
FIG. 14 is a fragmentary view of a further wire layout in accordance with the present invention.
Figure 15:
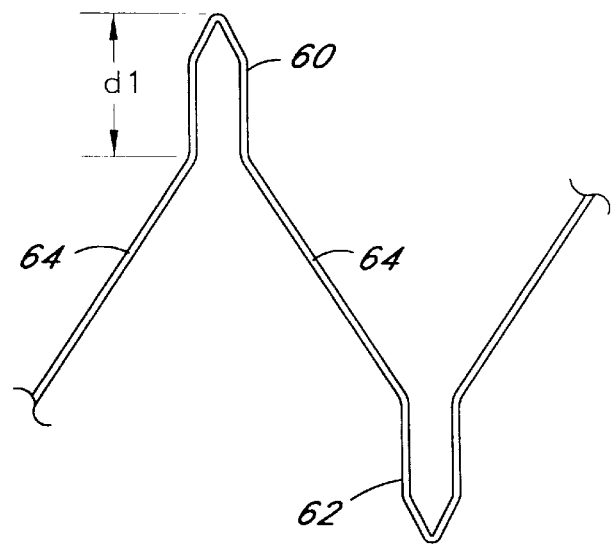
FIG. 15 is a fragmentary view of a further wire layout in accordance with the present invention.
Figure 16:
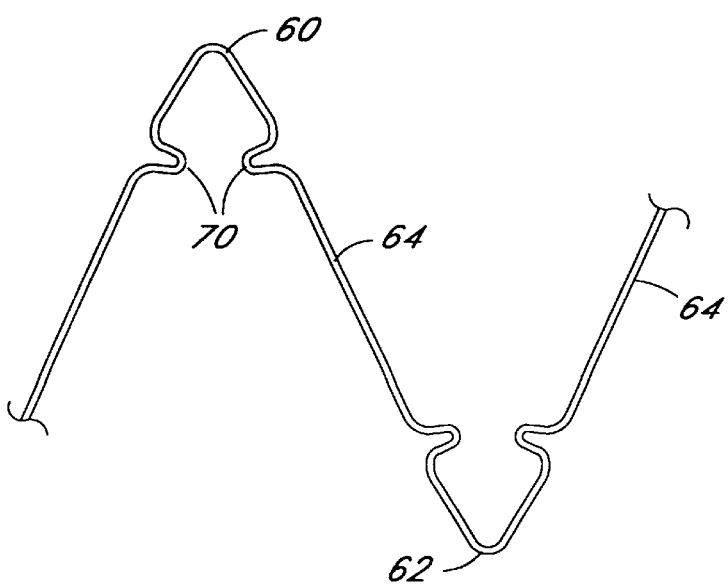
FIG. 16 is a fragmentary view of a further wire layout in accordance with the present invention.

Additional embodiments of the wire configuration are illustrated in FIGS. 14–16. FIG. 14 shows an embodiment of the proximal 60 and distal 62 bends in which double bends are employed to increase the flexion. Alternatively, FIG. 15 shows triangular bends having a more pronounced length (d1) of parallel wire, and accordingly shorter wall sections 64. Another embodiment of the proximal and distal bends is shown in FIG. 16, wherein the triangular bends include additional flexion points in the form of wall segment bends 70.

Referring to FIGS. 17 and 18, a deployment device and method in accordance with a preferred embodiment of the present invention are illustrated. A delivery catheter 80, having a dilator tip 82, is advanced along guidewire 84 until the (anatomically) proximal end 50 of the collapsed endoluminal vascular prosthesis 86 is positioned between the renal arteries 32 and 34 and the aneurysm 40. The collapsed prosthesis in accordance with the present invention has a diameter in the range of about 2 to about 10 mm. Preferably, the diameter of the collapsed prosthesis is in the range of about 3 to 6 mm (12 to 18 French). More preferably, the delivery catheter including the prosthesis will be 16 F, or 15 F or 14 F or smaller.

Figure 19:
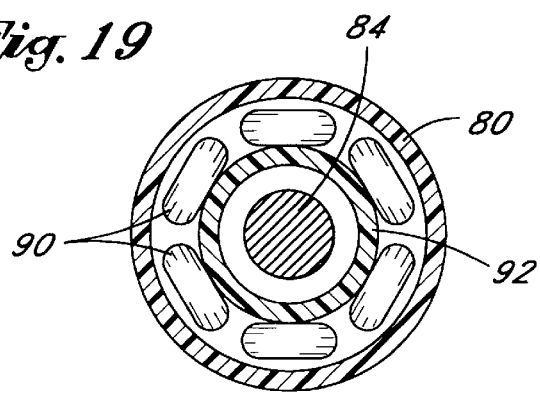
FIG. 19 is a cross sectional view taken along the lines 19—19 of FIG. 17.

The prosthesis 86 is maintained in its collapsed configuration by the restraining walls of the tubular delivery catheter 80, such that removal of this restraint would allow the prosthesis to self expand. Radiopaque marker material may be incorporated into the delivery catheter 80, and/or the prosthesis 86, at least at both the proximal and distal ends, to facilitate monitoring of prosthesis position. The dilator tip 82 is bonded to an internal catheter core 92, as illustrated in FIG. 18, wherein the internal catheter core 92 and the partially expanded prosthesis 88 are revealed as the outer sheath of the delivery catheter 80 is retracted. The internal catheter core 92 is also depicted in the cross-sectional view in FIG. 19.

As the outer sheath is retracted, the collapsed prosthesis 86 remains substantially fixed axially relative to the internal catheter core 92 and consequently, self-expands at a predetermined vascular site as illustrated in FIG. 18. Continued retraction of the outer sheath results in complete deployment of the graft. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

In addition to, or in place of, the outer sheath described above, the prosthesis 86 may be maintained in its collapsed configuration by a restraining lace, which may be woven through the prosthesis or wrapped around the outside of the prosthesis in the collapsed reduced diameter. Following placement of the prosthesis at the treatment site, the lace can be proximally retracted from the prosthesis thereby releasing it to self expand at the treatment site. The lace may comprise any of a variety of materials, such as sutures, strips of PTFE, FEP, polyester fiber, and others as will be apparent to those of skill in the art in view of the disclosure herein. The restraining lace may extend proximally through a lumen in the delivery catheter or outside of the catheter to a proximal control. The control may be a pull tab or ring, rotatable reel, slider switch or other structure for permitting proximal retraction of the lace. The lace may extend continuously throughout the length of the catheter, or may be joined to another axially moveable element such as a pull wire.

In general, the expanded diameter of the graft in accordance with the present invention can be any diameter useful for the intended lumen or hollow organ in which the graft is to be deployed. For most arterial vascular applications, the expanded size will be within the range of from about 10 to about 40 mm. Abdominal aortic applications will generally require a graft having an expanded diameter within the range of from about 20 to about 28 mm, and, for example, a graft on the order of about 45 mm may be useful in the thoracic artery. The foregoing dimensions refer to the expanded size of the graft in an unconstrained configuration, such as on the table. In general, the graft will be positioned within an artery having a slightly smaller interior cross section than the expanded size of the graft. This enables the graft to maintain a slight positive pressure against the wall of the artery, to assist in retention of the graft during the period of time prior to endothelialization of the polymeric sleeve 44.

Figure 20:
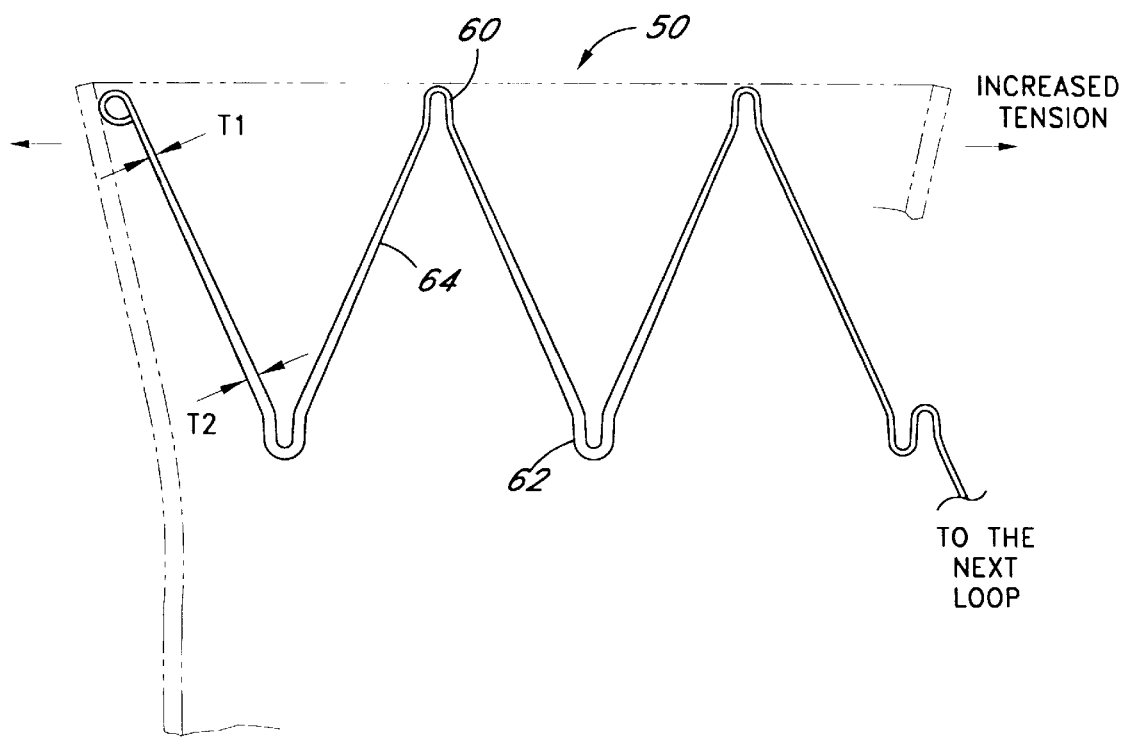
FIG. 20 is a detailed fragmentary view of a tapered wire embodiment in accordance with a further aspect of the present invention.

The radial force exerted by the proximal segment 94 of the prosthesis against the walls of the aorta 30 provides a seal against the leakage of blood around the vascular prosthesis and tends to prevent axial migration of the deployed prosthesis. As discussed above, this radial force can be modified as required through manipulation of various design parameters, including the axial length of the segment and the bend configurations. In another embodiment of the present invention, radial tension can be enhanced at the proximal, upstream end by changes in the wire gauge as illustrated in FIG. 20. Note that the wire gauge increases progressively along the wall segments 64 from T1 at the proximal bends 60 to T2 at the distal bends 62. Consequently, the radial flex exerted by the distal bends 62 is greater than that exerted by the proximal bends 60 and the radial tension is thereby increased at the proximal end 50 of the prosthesis. T1 may range from about 0.001 to 0.01 inches whereas T2 may range from about 0.01 to 0.03 inches.

An alternative embodiment of the wire layout which would cause the radial tension to progressively decrease from the proximal segments to the distal segments, involves a progressive or step-wise decrease in the wire gauge throughout the entire wire support, from about 0.01 to 0.03 inches at the proximal end to about 0.002 to 0.01 inches at the distal end. Such an embodiment, may be used to create a tapered prosthesis. Alternatively, the wire gauge may be thicker at both the proximal and distal ends, in order to insure greater radial tension and thus, sealing capacity. Thus, for instance, the wire gauge in the proximal and distal segments may about 0.01 to 0.03 inches, whereas the intervening segments may be constructed of thinner wire, in the range of about 0.001 to 0.01 inches.

Figure 21:
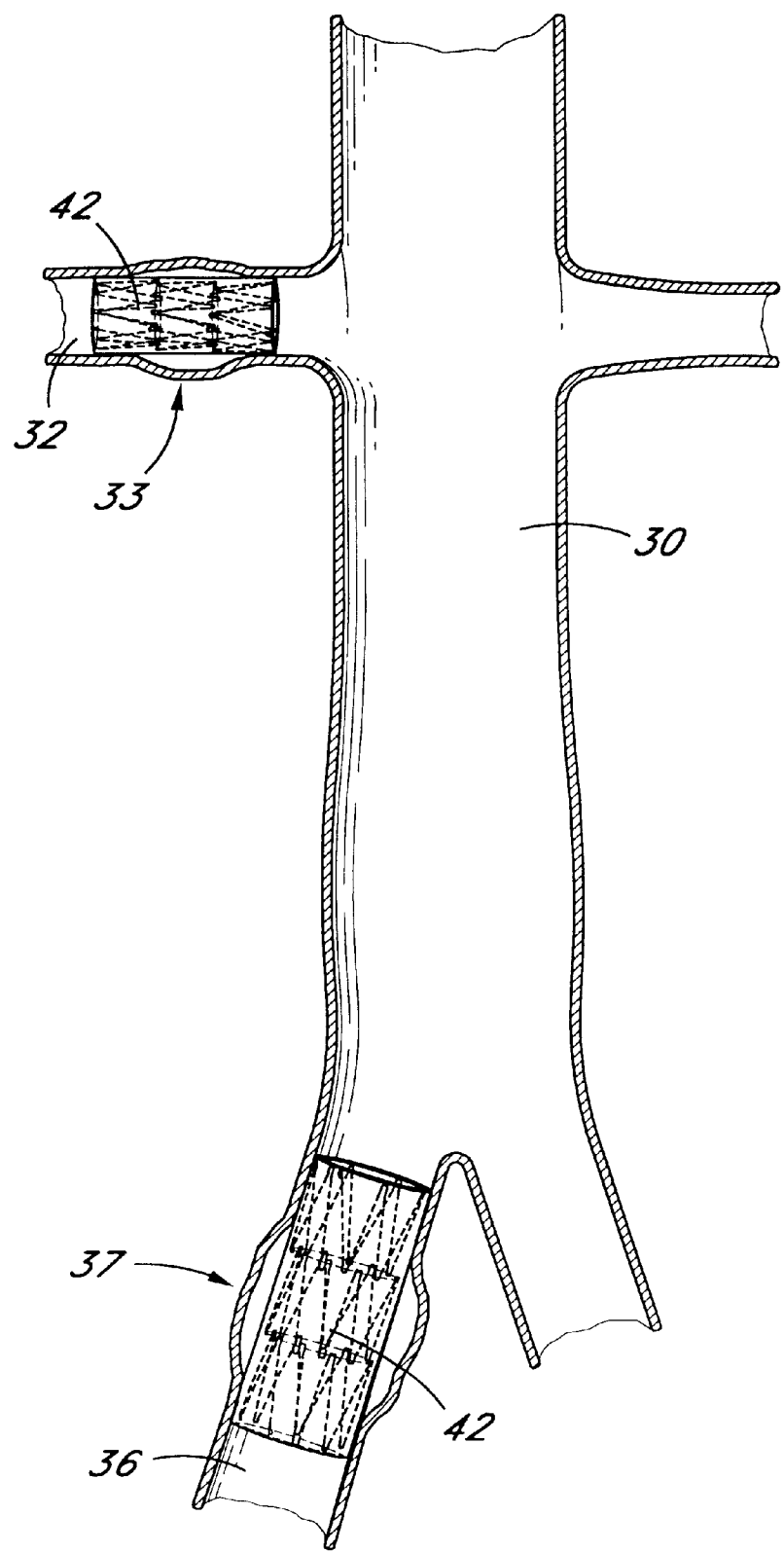
FIG. 21 is a schematic representation of the abdominal aortic anatomy, with an endoluminal vascular prosthesis of the present invention positioned within each of the right renal artery and the right common iliac.

Referring to FIG. 21, there is illustrated two alternative deployment sites for the endoluminal vascular prosthesis 42 of the present invention. For example, a symmetrical aneurysm 33 is illustrated in the right renal artery 32. An expanded endoluminal vascular prosthesis 42, in accordance with the present invention, is illustrated spanning that aneurysm 33. Similarly, an aneurysm of the right common iliac 37 is shown, with a prosthesis 42 deployed to span the iliac aneurysm 37.

Figure 22:
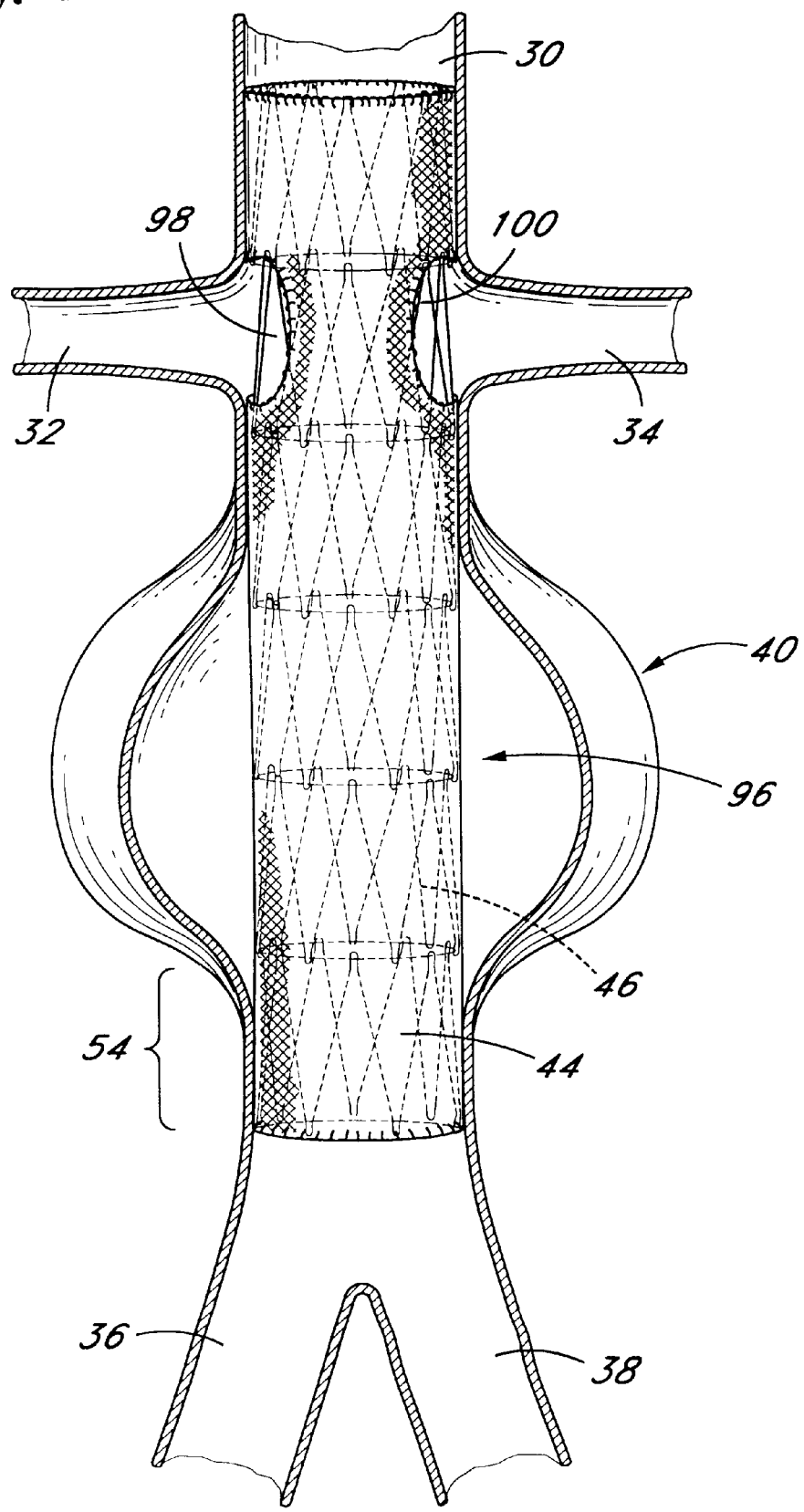
FIG. 22 is a modified embodiment of the prosthesis in accordance with the present invention.

Referring to FIG. 22, there is illustrated a modified embodiment of the endovascular prosthesis 96 in accordance with the present invention. In the embodiment illustrated in FIG. 22, the endovascular prosthesis 96 is provided with a wire cage 46 having six axially aligned segments 54. As with the previous embodiments, however, the endovascular prosthesis 96 may be provided with anywhere from about 2 to about 10 or more axially spaced or adjacent segments 54, depending upon the clinical performance objectives of the particular embodiment.

The wire support 46 is provided with a tubular polymeric sleeve 44 as has been discussed. In the present embodiment, however, one or more lateral perfusion ports or openings are provided in the polymeric sleeve 44, such as a right renal artery perfusion port 98 and a left renal artery perfusion port 100 as illustrated.

Perfusion ports in the polymeric sleeve 44 may be desirable in embodiments of the endovascular prosthesis 96 in a variety of clinical contexts. For example, although FIGS. 1 and 22 illustrate a generally symmetrical aneurysm 40 positioned within a linear infrarenal portion of the abdominal aorta, spaced axially apart both from bilaterally symmetrical right and left renal arteries and bilaterally symmetrical right and left common iliacs, both the position and symmetry of the aneurysm 40 as well as the layout of the abdominal aortic architecture may differ significantly from patient to patient. As a consequence, the endovascular prosthesis 96 may need to extend across one or both of the renal arteries in order to adequately anchor the endovascular prosthesis 96 and/or span the aneurysm 40. The provision of one or more lateral perfusion ports enables the endovascular prosthesis 96 to span the renal arteries while permitting perfusion therethrough, thereby preventing "stent jailing" of the renals. Lateral perfusion through the endovascular prosthesis 96 may also be provided, if desired, for a variety of other arteries including the second lumbar, testicular, inferior mesenteric, middle sacral, and alike as will be well understood to those of skill in the art.

The endovascular prosthesis 96 is preferably provided with at least one, and preferably two or more radiopaque markers, to facilitate proper positioning of the prosthesis 96 within the artery. In an embodiment having perfusion ports 98 and 100 such as in the illustrated design, the prosthesis 96 should be properly aligned both axially and rotationally, thereby requiring the ability to visualize both the axial and rotational position of the device. Alternatively, provided that the delivery catheter design exhibits sufficient torque transmission, the rotational orientation of the graft maybe coordinated with an indexed marker on the proximal end of the catheter, so that the catheter may be rotated and determined by an external indicium of rotational orientation to be appropriately aligned with the right and left renal arteries.

In an alternative embodiment, the polymeric sleeve 44 extends across the aneurysm 40, but terminates in the infrarenal zone. In this embodiment, a proximal zone 55 on the prosthesis 96 comprises a wire cage 46 but no polymeric sleeve 44. In this embodiment, the prosthesis 96 still accomplishes the anchoring function across the renal arteries, yet does not materially interfere with renal perfusion. Thus, the polymeric sleeve 44 may cover anywhere from about 50% to about 100% of the axial length of the prosthesis 96 depending upon the desired length of uncovered wire cage 46 such as for anchoring and/or lateral perfusion purposes. In particular embodiments, the polymeric sleeve 44 may cover within the range of from about 70% to about 80%, and, in one four segment embodiment having a single exposed segment, 75%, of the overall length of the prosthesis 96. The uncovered wire cage 46 may reside at only a single end of the prosthesis 96, such as for traversing the renal arteries. Alternatively, exposed portions of the wire cage 46 may be provided at both ends of the prosthesis such as for anchoring purposes.

In a further alternative, a two part polymeric sleeve 44 is provided. A first distal part spans the aneurysm 40, and has a proximal end which terminates distally of the renal arteries. A second, proximal part of the polymeric sleeve 44 is carried by the proximal portion of the wire cage 46 which is positioned superiorly of the renal arteries. This leaves an annular lateral flow path through the side wall of the vascular prosthesis 96, which can be axially aligned with the renal arteries, without regard to rotational orientation.

The axial length of the gap between the proximal and distal segments of polymeric sleeve 44 can be adjusted, depending upon the anticipated cross sectional size of the ostium of the renal artery, as well as the potential axial misalignment between the right and left renal arteries. Although the right renal artery 32 and left renal artery 34 are illustrated in FIG. 22 as being concentrically disposed on opposite sides of the abdominal aorta, the take off point for the right or left renal arteries from the abdominal aorta may be spaced apart along the abdominal aorta as will be familiar to those of skill in the art. In general, the diameter of the ostium of the renal artery measured in the axial direction along the abdominal aorta falls within the range of from about 7 cm to about 20 cm for a typical adult patient.

Clinical and design challenges, which are satisfied by the present invention, include providing a sufficient seal between the upstream end of the vascular prosthesis and the arterial wall, providing a sufficient length to span the abdominal aortic aneurysm, providing sufficient wall strength or support across the span of the aneurysm, and providing a sufficient expansion ratio, such that a minimal percutaneous axis diameter may be utilized for introduction of the vascular prosthesis in its collapsed configuration.

Prior art procedures presently use a 7 mm introducer (18 French) which involves a surgical procedure for introduction of the graft delivery device. In accordance with the present invention, the introduction profile is significantly reduced. Embodiments of the present invention can be constructed having a 16 French or 15 French or 14 French or smaller profile (e.g. 3–4 mm) thereby enabling placement of the endoluminal vascular prosthesis of the present invention by way of a percutaneous procedure. In addition, the endoluminal vascular prosthesis of the present invention does not require a post implantation balloon dilatation, can be constructed to have minimal axial shrinkage upon radial expansion, and avoids the disadvantages associated with nitinol grafts.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. An endoluminal prosthesis, comprising:
a tubular wire support comprising at least first and second axially adjacent tubular segments joined by a connector extending therebetween, wherein the first and second tubular segments and the connector are formed from a single length of wire, and wherein each tubular segment comprises a series of proximal and distal bends, such that each proximal bend in the first tubular segment aligns with a distal bend in the second tubular segment to form a joint;
wherein each joint includes an eye.

2. The endoluminal prosthesis of claim 1, wherein the eye is a circular loop.

3. The endoluminal prosthesis of claim 2, wherein the eye is a double-looped circular eye.

4. The endoluminal prosthesis of claim 1, wherein the eye is a double-looped triangular eye.

5. An endoluminal prosthesis as in claim 1, comprising at least three segments and two connectors.

6. An endoluminal prosthesis as in claim 1, comprising at least five segments and four connectors.

7. An endoluminal prosthesis as in claim 1, wherein the wire in each segment comprises a series of strut segments connecting the proximal bends and distal bends to form a tubular segment wall.

8. An endoluminal prosthesis as in claim 7, wherein at least some of the strut segments are substantially linear.

9. An endoluminal prosthesis as in claim 7, wherein each segment comprises from about 4 proximal bends to about 12 proximal bends.

10. An endoluminal prosthesis as in claim 1, having at least a proximal segment, an intermediate segment and a distal segment, wherein the prosthesis is expandable from a reduced cross section to an expanded cross section.

11. An endoluminal prosthesis as in claim 10, wherein at least a portion of the proximal segment and distal segment is larger in cross section than the central segment when the prosthesis is in the expanded cross section.

12. An endoluminal prosthesis as in claim 1, further comprising a polymeric layer on the wire support.

13. An endoluminal prosthesis as in claim 12, wherein the layer comprises a tubular PTFE sleeve surrounding at least a central portion of the prosthesis.

14. An endoluminal prosthesis as in claim 1, wherein the first tubular segment has a different radial strength than the second tubular segment.

15. An endoluminal prosthesis as in claim 14, further comprising a third tubular segment, wherein at least one of the tubular segments has a different radial strength than the other two tubular segments.

16. An endoluminal prosthesis as in claim 15, wherein a proximal end of the prosthesis is self expandable to a greater diameter than a central region of the prosthesis.

17. An endoluminal prosthesis as in claim 13, wherein the sleeve further comprises at least one lateral perfusion port extending therethrough.

18. An endoluminal prosthesis as in claim 1, wherein the joint comprises a pivotable connection.

19. An endoluminal prosthesis as in claim 1, wherein the joint comprises a metal link.

20. An endoluminal prosthesis as in claim 1, wherein the joint comprises a suture.

21. An endoluminal prosthesis as in claim 1, wherein the prosthesis has an expansion ratio of at least about 1:4.

22. An endoluminal prosthesis as in claim 21, wherein the prosthesis has an expansion ratio of at least about 1:5.

23. An endoluminal prosthesis as in claim 12, wherein the prosthesis has an expanded diameter of at least about 20 mm in an unconstrained expansion, and the prosthesis is implantable using a catheter no greater than about 16 French.

24. A prosthesis as in claim 12, wherein the prosthesis has an expanded diameter of at least about 25 mm, and is implantable on a delivery device having a diameter of no more than about 16 French.

25. An endoluminal prosthesis, comprising:
a tubular wire support comprising at least first and second axially adjacent tubular segments joined by a connector extending therebetween, wherein the first and second tubular segments and the connector are formed from a single length of wire, and wherein each tubular segment comprises a series of proximal and distal bends, such that each proximal bend in the first tubular segment aligns with a distal bend in the second tubular segment to form a joint;
wherein each joint includes an eye in the form of a circular loop of wire.

26. The endoluminal prosthesis of claim 25, wherein the eye is a double-looped triangular eye.

27. An endoluminal prosthesis as in claim 25, comprising at least three segments and two connectors.

28. An endoluminal prosthesis as in claim 25, comprising at least five segments and four connectors.

29. An endoluminal prosthesis as in claim 25, wherein the wire in each segment comprises a series of strut segments connecting the proximal bends and distal bends to form a tubular segment wall.

30. An endoluminal prosthesis as in claim 29, wherein at least some of the strut segments are substantially linear.

31. An endoluminal prosthesis as in claim 29, wherein each segment comprises from about 4 proximal bends to about 12 proximal bends.

32. An endoluminal prosthesis as in claim 25, having at least a proximal segment, an intermediate segment and a distal segment, wherein the prosthesis is expandable from a reduced cross section to an expanded cross section.

33. An endoluminal prosthesis as in claim 32, wherein at least a portion of the proximal segment and distal segment is larger in cross section than the central segment when the prosthesis is in the expanded cross section.

34. An endoluminal prosthesis as in claim 25, further comprising a polymeric layer on the wire support.

35. An endoluminal prosthesis as in claim 34, wherein the layer comprises a tubular PTFE sleeve surrounding at least a central portion of the prosthesis.

36. An endoluminal prosthesis as in claim 25, wherein the first tubular segment has a different radial strength than the second tubular segment.

37. An endoluminal prosthesis as in claim 36, further comprising a third tubular segment, wherein at least one of the tubular segments has a different radial strength than the other two tubular segments.

38. An endoluminal prosthesis as in claim 37, wherein a proximal end of the prosthesis is self expandable to a greater diameter than a central region of the prosthesis.

39. An endoluminal prosthesis as in claim 35, wherein the sleeve further comprises at least one lateral perfusion port extending therethrough.

40. An endoluminal prosthesis as in claim 25, wherein the joint comprises a pivotable connection.

41. An endoluminal prosthesis as in claim 25, wherein the joint comprises a metal link.

42. An endoluminal prosthesis as in claim 25, wherein the joint comprises a suture.

43. An endoluminal prosthesis as in claim 25, wherein the prosthesis has an expansion ratio of at least about 1:4.

44. An endoluminal prosthesis as in claim 43, wherein the prosthesis has an expansion ratio of at least about 1:5.

45. An endoluminal prosthesis as in claim 34, wherein the prosthesis has an expanded diameter of at least about 20 mm in an unconstrained expansion, and the prosthesis is implantable using a catheter no greater than about 16 French.

46. A prosthesis as in claim 34, wherein the prosthesis has an expanded diameter of at least about 25 mm, and is implantable on a delivery device having a diameter of no more than about 16 French.

\* \* \* \* \*